United States Patent [19]

Kursar

[11] Patent Number: 5,179,953
[45] Date of Patent: Jan. 19, 1993

[54] PORTABLE DIURNAL INTRAOCULAR PRESSURE RECORDING SYSTEM

[75] Inventor: Gerald H. Kursar, Des Peres, Mo.

[73] Assignee: Jermik Systems, Ltd., St. Louis, Mo.

[21] Appl. No.: 750,528

[22] Filed: Aug. 27, 1991

[51] Int. Cl.⁵ .............................................. A61B 3/16
[52] U.S. Cl. ..................................... 128/645; 128/646
[58] Field of Search ............... 128/645, 646, 650, 651, 128/652

[56] References Cited

U.S. PATENT DOCUMENTS 4,922,913 5/1990 Waters, Jr. et al. ................ 128/645

Primary Examiner—Randy C. Shay
Attorney, Agent, or Firm—Eugene E. Renz, Jr.

[57] ABSTRACT

A device for continuously monitoring the intraocular pressure in an eye, which includes a scleral contact lens having a pressure transducer thereon for measuring intraocular pressure. The lens is sized to fit within the sclera of an eye for positioning the pressure transducer in fixed contact with the sclera in the superior temporal quadrant of the eye in the superior cul-de-sac during movement of the eye. The pressure transducer includes at least one semiconductor strain gauge crystal adapted to generate an electrical resistance which is responsive to inraocular pressure. A projection is provided for scleral indentation and is positioned to transmit response to intracular pressure to the crystal. A battery powered memory unit is mounted in the lens in non-scleral contact for recording measurements of pressure by the transducer over a predetermined period of time, preferably by, measuring the resistance through the crystal. The crystal is fixed to a flexible membrane forming a mounting on the contact lens. Output is obtained by providing access to the measurements stored in the memory unit upon removal of the lens from the eye.

4 Claims, 2 Drawing Sheets

PORTABLE DIURNAL INTRAOCULAR PRESSURE RECORDING SYSTEM

FIELD OF THE INVENTION

The present invention relates to a device for recording the intraocular pressure of a person or animal over a period of time. More particularly, the invention relates to a device which can be placed in the eye to continuously monitor and record intraocular pressure over an extended period of time such as 24 hours or more.

BACKGROUND OF THE INVENTION

Three to four million persons in the United States suffer from glaucoma to some degree, although only about half of these persons are treated by routine administration of glaucoma medication. Glaucoma is recognized to be the leading cause of blindness in this country.

Typical treatment for glaucoma to reduce the excessive intraocular pressure involves the administration of drugs which operate on the intraocular pressure. These drugs do not have a long term straight line effect on intraocular pressure, however, and individual treatments may be more or less effective at any particular period of time in the treatment cycle. For most glaucoma cases, intraocular pressure varies throughout the day, usually reaching its peak about 3:00 am. This diurnal cycle presents difficulties to the attending physician, who sees the patient at only one relatively short period of time. For this reason, it is difficult for the practitioner to accurately assess the effect of glaucoma medications.

At the present time, there is recognition that the cycle of intraocular pressure is diurnal and is subject to several variables. However, no acceptable means presently exists to continuously measure intraocular pressure.

One such means has been proposed in U.S. Pat. No. 4,089,329, to Couvillon et al, in which a contact lens is used to maintain vision for the patient. The patent notes, however, that sensitivity of the cornea to the device presents a serious problem. To solve this problem, a miniature strain gauge pressure transducer is used, in the form of a noncompliant, planar diaphragm for applanating a small portion of the sclera. A hydrogel ring is placed within the conjunctival cul-de-sac of the eye in a concentric orientation with the cornea to permit vision during the process.

In the Couvillon et al device, separation of tissue supplies the necessary force to the transducer diaphragm to applanate the contacted portion of the sclera. The resultant stress, monitored as resistance variations, is sent to a transmitter via connecting wires. While the Couvillon et al patent does not say so explicitly, the wires appear to extend from the hydrogel ring to a transmitter which is external to the eye. Signals are sent to a receiver/transcriber for analysis and use in other ways.

The Couvillon et al device contemplates the use of a ring platform, made preferably from hydrogel. The ring must be sufficient to allow eye movement without serious contact with corneal tissue. Wire conductors convey the current from the strain gauges, and change in resistance is measured as change in voltage. As noted in the description of the "communicating means" described in the Detailed Description of the Couvillon et al patent, the transmitter is fixed to the patient's glasses or person. Presumably, preventative methods are in place to prevent the patient from removing his or her glasses with the ring platform still in the eye and attached to the transmitter via the wire conductors.

SUMMARY OF THE INVENTION

It has now been discovered that the above and other objects of the present invention may be accomplished in the following manner. Specifically, the present invention provides a device for continuously monitoring the intraocular pressure in an eye.

The device includes a scleral contact lens having a pressure transducer thereon for measuring intraocular pressure and sized to fit within the sclera of an eye for positioning said pressure transducer in fixed contact with said sclera during movement of said eye. The transducer includes projection means for scleral indentation, as the projection operates in response to the actual intraocular pressure. In a preferred embodiment, the pressure transducer includes at least one semiconductor strain gauge crystal adapted to generate an electrical resistance which is responsive to intraocular pressure.

Also included are battery powered memory means mounted in said lens in non-scleral contact for recording measurements of pressure by said transducer over a predetermined period of time. Naturally, the data which is stored in the memory means is used to evaluate the changes, if any, of pressure in the eye for various reason. Output means such as a central processing unit or computer is used for this evaluation. The device itself has connecting means for providing access to said measurements upon removal of said lens from the eye. Data can be displayed in graphic form, on screen or on paper, depending on the needs of the practitioner.

The device of this invention is self contained and can be worn by a patient with minimal or no discomfort. The battery powered memory means, in the form of an integrated circuit chip, supplies a small current to the crystal, so that the resistance through said crystal is representative of the intraocular pressure. The crystal is fixed to a flexible membrane forming mounting means on said contact lens.

In the preferred embodiment, the scleral contact lens is designed to locate the transducer in the superior temporal quadrant of the eye in the superior cul-de-sac. Other locations are also contemplated.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Figure 1:
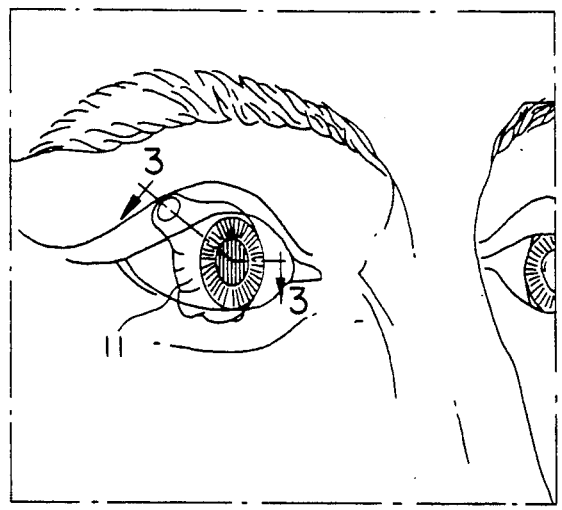
FIG. 1 is a schematic view of a device according to the present invention, shown in place on a human eye.

As shown in FIG. 1, the device of this invention is placed in a patient's eye in order to measure and record intraocular pressure over a period of time. The device of the present invention includes a large scleral contact lens made of silicone or polymethylmethacrylate, for example. The contact lens 11 is shown in FIG. 1 in place in a patient's eye, and is comfortable and easy to wear without significant discomfort for the patient. The lens is soft, and ring shaped 13, and approximately 18 mm in diameter, with a 13.5 mm opening 15 in the center.

The lens 11 permits movement of the eye while maintaining the operable components in a fixed position. As will be apparent herein, movement of the lens with respect to the eye could give the feeling of scratching or other discomfort due to the presence of a pressure tranducer in contact with the sclera of the eye.

Figure 2:
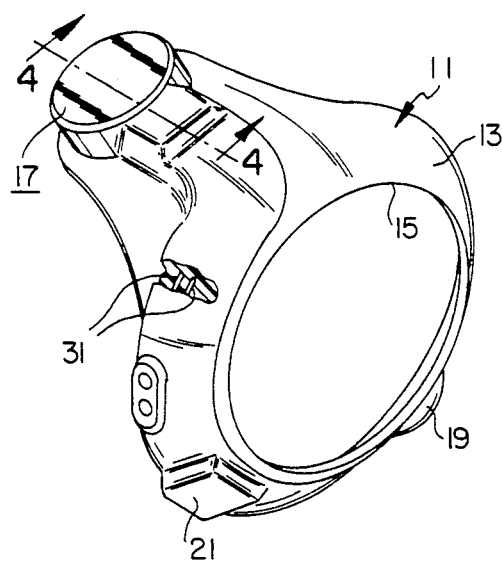
FIG. 2 is an enlarged view of the device shown in FIG. 1, removed from the eye.

The lens 11 is shown in FIG. 2, and includes a ring 13 which has an outer circumferential end 15 which prevents contact of the lens with the cornea and allows for complete vision without obstruction. The open center 15 of the lens 11 allows normal visual activities and also permits normal adsorption of medications during the time the lens is in use. The system is non-invasive and can be comfortably worn by the patient. No restrictions are placed on the patent when the device of this invention is in use.

Forming part of the lens 11 is a pressure transducer 17 which is located for contact with the sclera. This transducer 17 monitors the intraocular pressure continuously or at regular intervals of time, depending upon the needs of the practitioner.

The pressure transducer 17 is mounted on a flange of the ring 13 with a 8 mm projection preferably extending into the superior temporal quadrant of the eye. Both right and left hand models will be needed, along with two overall sizes to fit normal and large eyes. The inferior margin of the contact lens 11 is truncated or flattened in order to position the transducer 17 in the inferior cul-de-sac. This alignment prevents rotation and keeps the transducer 17 in the desired location. Transducer 17 is powered by electrical current from battery 19 which is also mounted on the lens 11. The sclera is readily exposed to indention by the transducer at this location, as the tissues are relatively thin in this area and there are no extraocular muscles to interfere with indention. The area is also broad, allowing for some normal positional changes.

Battery 19 is operably connected to the transducer in order to power the pressure measuring component of the device. Memory chip 21 is also connected to battery 19 and to transducer 17 to receive and store data taken during operation of the device. Chip 21 is of conventional design.

Figure 3:
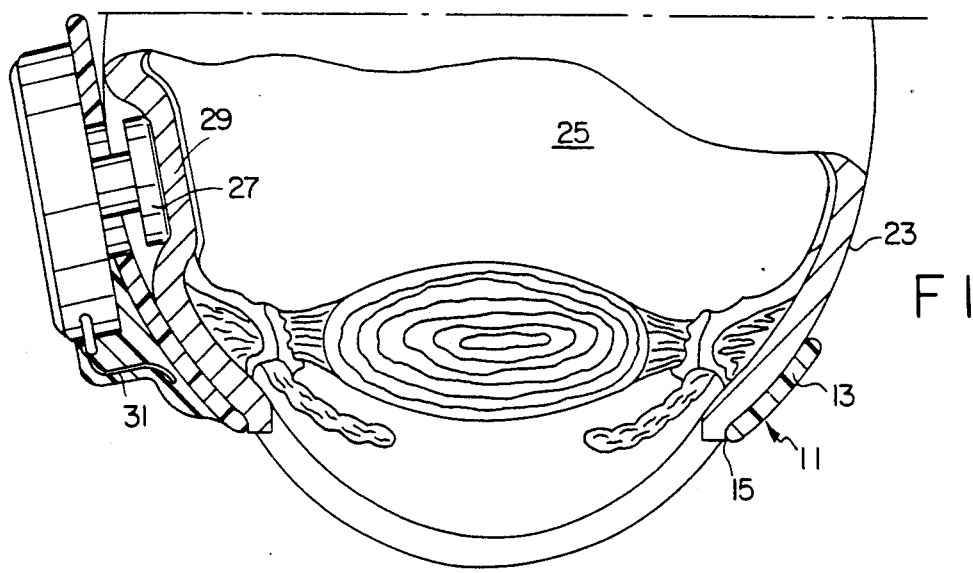
FIG. 3 is an enlarged sectional plan view taken along line 3,3 of FIG. 1.

The device of this invention is shown in enlarged detail in FIG. 3, which has been magnified approximately 6 times the size of a normal eye. The ring 13 rests comfortably on the sclera 23 of the eye and permits the transducer to measure the intraocular pressure at 25.

The sclera 23 of the eye is indented by pressing the apex of a mushroom shaped projection 27 into the appropriate region 29 of sclera 23. Projection 27 moves in response to pressure and changes in pressure in the intraocular region 25 to provide the needed data. Electrical power for the transducer 17 and for transmission of data is accomplished via small electrically conductive insulated wires 31. All electrical and electronic components are inbeded in a water proof shroud.

Figure 4:
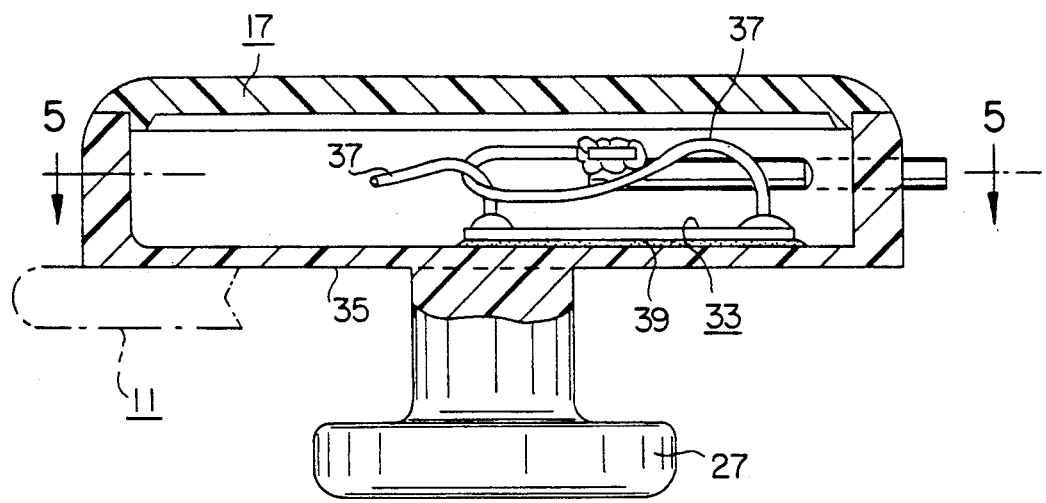
FIG. 4 is a greatly enlarged sectioned view taken along the line 4,4 of FIG. 2, showing details of the transducer portion of the device of this invention, with a small portion of the mounting flange shown in dot and dash outline.
Figure 5:
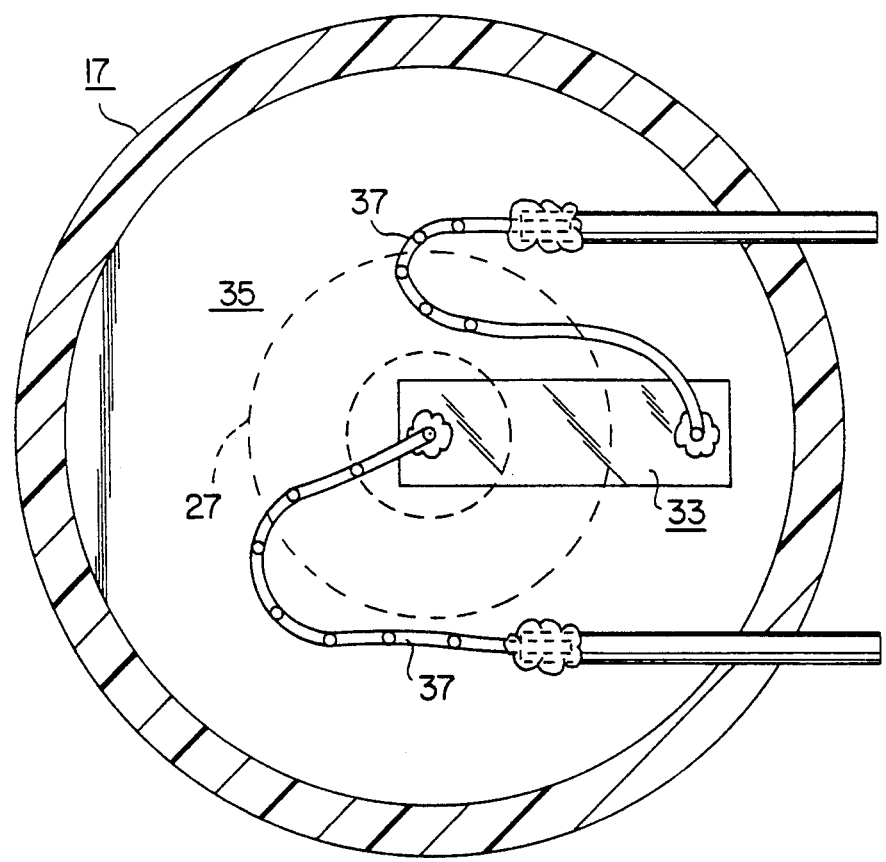
FIG. 5 is a sectional plan view taken along line 5,5 of FIG. 4, showing additional details of the transducer assembly.

As shown in FIG. 4 and FIG. 5, the projection 27 of about 3.5 mm in size is operably connected to a semiconductor strain gauge crystal 33, such as those used in automatic blood pressure devices. In one embodiment, a 1×2.5 mm crystal 33 with a nominal resistance of 1125 ohms was attached to a flexible membrane 35 by means of epoxy 39 Thin leads 37 were attached to both ends of crystal 33.

As current flows through the crystal 33, the memory chip 21 records the resistance in the crystal. As pressure changes in the intraocular region 25, the projection 27 reacts to this change in pressure to increase or decrease the bending moment on crystal 33, thus changing the resistance of the crystal.

Once the lens has been placed in the eye, a period of stabilization is needed. It has been noted that there will be a temporary rise in intraocular pressure as the device is applied to the globe by decreasing the volume of fluid within the globe. This will cause an initial increase in the intraocular pressure. Depending upon the outflow resistance of that particular patient, this excess fluid will be forced out of the eye though the trabecular network and the pressure within the eye will stabilize. This is reached when the pre-application and post-application IOP are the same. Experience suggests that this takes about 5 minutes to be achieved.

As the pressure within the eye changes, scleral indention will be greater or less. The distance between the base of the transducer and the face of the mushroom shaped projection 27 which is attached to the crystal 33 via membrane 35 will respond and be greater or less. This is measured as described above by recording the change in resistance in the crystal 33.

The stored data can then be withdrawn from memory chip 21 and processed with computer technology to convert resistance values into pressure. Since the initial pressure can also be measured independently at the time when the lens is inserted into the eye and when it is removed, such as by applanation tonometric measurements. Also, while the patient is still with the practitioner, additional applanation measurements can be made to verify stabilization of the intraocular pressure. The patient is now free to continue with normal activity for the period of time of testing. Typically, 24 hours is sufficient to obtain adequate data.

In order to demonstrate the operability and effectiveness of the device of the present invention, a series of tests were made in a laboratory setting. Intraocular pressure in an animal cadaver eye was varied over a range of pressure from about 10 mm Hg. up to about 55 mm Hg. by varying the height of a bottle containing fluid and connected to the eye. The results of the tests demonstrated that linear and repeatable data was attainable using the device of this invention. In actual practice, a printout of the data recording the intraocular pressure in the eye can be correlated with the times when medication is administered, to evaluate the effectiveness of the prescribed treatment program. The printout would also provide a permanent assurance of the safety of any external pressure applied to the eye.

While particular embodiments of the present invention have been illustrated and described, it is not intended to limit the invention, except as defined by the following claims.

I claim:

1. A device for continuously monitoring the intraocular pressure in an eye, comprising:
   a scleral contact lens having a pressure transducer thereon for measuring intraocular pressure and sized to fit within the sclera of an eye and position said pressure transducer in fixed contact with said sclera to indent said sclera in the superior temporal quadrant of the eye in the superior cul-de-sac during movement of said eye, said pressure transducer including at least one semiconductor strain gauge crystal adapted to vary its electrical resistance in response to intraocular pressure and projection means for positive scleral indentation, said projection means being positioned to transmit a response to intraocular pressure to said crystal;
   battery powered memory means mounted in said lens in non-scleral contact for recording measurements of the resistance through said crystal; and
   output means for providing access to said measurements upon removal of said lens from the eye.

2. The device of claim 1, wherein said battery powered memory means includes means for measuring the resistance through said crystal, said crystal being fixed to a flexible membrane forming mounting means on said contact lens.

3. A method for continuously monitoring the intraocular pressure in an eye, comprising:
   placing a scleral contact lens having a pressure transducer thereon for measuring intraocular pressure within the sclera of an eye in fixed contact to indent said sclera in the superior temporal quadrant of the eye in the superior cul-de-sac during movement of said eye, said pressure transducer including at least one semiconductor strain gauge crystal adapted to vary its electrical resistance in response to intraocular pressure and projection means for positive scleral indentation, said projection means being positioned to transmit a response to intraocular pressure to said crystal;
   recording measurements of the resistance through said crystal using a battery powered memory means mounted in said lens in non-scleral contact; and
   providing access to said measurements upon removal of said lens from the eye.

4. The method of claim 3, wherein said battery powered memory means measures the resistance through said crystal, said crystal being fixed to a flexible membrane mounting said crystal on said contact lens.

* * * * *